United States Patent
Pearl et al.

(10) Patent No.: US 9,829,440 B2
(45) Date of Patent: Nov. 28, 2017

(54) IN-SITU MONITORING OF RECOMBINATION PROGRESS USING ICE

(71) Applicant: Halliburton Energy Services, Inc., Houston, TX (US)

(72) Inventors: Megan Renee Pearl, Houston, TX (US); William Cecil Pearl, Jr., Houston, TX (US); Juliana Midori Matsushita, Rio de Janeiro (BR)

(73) Assignee: Halliburton Energy Services, Inc., Houston, TX (US)

( * ) Notice: Subject to any disclaimer, the term of this patent is extended or adjusted under 35 U.S.C. 154(b) by 2 days.

(21) Appl. No.: 15/030,821

(22) PCT Filed: Dec. 11, 2013

(86) PCT No.: PCT/US2013/074435
§ 371 (c)(1),
(2) Date: Apr. 20, 2016

(87) PCT Pub. No.: WO2015/088518
PCT Pub. Date: Jun. 18, 2015

(65) Prior Publication Data
US 2016/0258875 A1    Sep. 8, 2016

(51) Int. Cl.
*G01N 21/84* (2006.01)
*E21B 49/08* (2006.01)
*G01N 33/28* (2006.01)
*E21B 47/00* (2012.01)

(52) U.S. Cl.
CPC ............ *G01N 21/84* (2013.01); *E21B 49/08* (2013.01); *E21B 49/087* (2013.01); *G01N 33/2823* (2013.01); *E21B 47/00* (2013.01); *G01N 2021/8405* (2013.01)

(58) Field of Classification Search
CPC .......................... G01N 21/84; G01N 33/2823
USPC ......................................................... 356/70
See application file for complete search history.

(56) References Cited

U.S. PATENT DOCUMENTS

| | | | | |
|---|---|---|---|---|
| 5,540,087 | A * | 7/1996 | Bickert | G01N 25/70 73/53.05 |
| 7,697,141 | B2 | 4/2010 | Jones et al. | |
| 8,212,216 | B2 | 7/2012 | Perkins et al. | |
| 8,213,006 | B2 | 7/2012 | Myrick et al. | |
| 8,237,920 | B2 | 8/2012 | Jones et al. | |
| 9,291,585 | B2 * | 3/2016 | Singh | G01N 25/00 |

(Continued)

FOREIGN PATENT DOCUMENTS

WO    2013048386    4/2013

OTHER PUBLICATIONS

International Search Report and Written Opinion of PCT Application No. PCT/US2013/074435 dated Aug. 21, 2015: pp. 1-15.

*Primary Examiner* — Roy M Punnoose
(74) *Attorney, Agent, or Firm* — Chamberlain Hrdlicka (57) ABSTRACT

An apparatus, method, and sample vessel for recombining a sample fluid. The sample fluid is received in a sample vessel. Sample parameters are recreated in the sample vessel. The sample fluid is agitated within the sample vessel. Optical measurements of the sample fluid are performed within the sample vessel utilizing one or more optical sensors. A determination is made whether recombination is complete in response to the optical measurements of the sample fluid performed by the one or more optical sensors.

10 Claims, 4 Drawing Sheets

(56) References Cited

U.S. PATENT DOCUMENTS

| | | |
|---|---|---|
| 2005/0146717 A1 | 7/2005 | Cerni |
| 2008/0178683 A1* | 7/2008 | Heathman ................ G01N 3/24 73/803 |
| 2013/0239664 A1 | 9/2013 | Hsu et al. |
| 2013/0243028 A1* | 9/2013 | Singh ..................... G01N 25/00 374/43 |
| 2013/0287061 A1 | 10/2013 | Freese et al. |

* cited by examiner

IN-SITU MONITORING OF RECOMBINATION PROGRESS USING ICE

BACKGROUND

The use of downhole samples during natural resource exploration has been increasingly utilized as a tool for analysis. For example, based on a downhole sample fluid, drilling and extraction strategies may be formulated, revised, or otherwise adjusted. In many cases, the downhole sample fluids separate from a single phase combination to a multiphase mixture when removed from the downhole environment. As a result, recombination systems, equipment, devices, and process may be utilized on all or a portion of the sample to simulate the downhole conditions.

The downhole sample fluid may be subsequently agitated or rocked to recombine the various fluids and gases into the original downhole composition. Whether the recombination process has been effective may be difficult to determine while the process is occurring and may require stopping the process to retrieve and test a sample. If testing reveals the original composition is not achieved, unknown additional process time and testing may be required. In addition, the downhole sample fluid may be agitated for too long wasting valuable time and delaying applicable information that may be utilized to produce the wellbore. Furthermore, inaccurate recombination in which the original downhole fluid composition is not achieved could lead to erroneous conclusions regarding production strategies employed at the wellbore.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE DRAWINGS

The illustrative embodiments provide an apparatus, system, method, agitator, and sample vessel for performing in situ monitoring of a recombination process utilizing optical sensors. In one embodiment, the optical sensor includes an integrated computational element (ICE) (also referred to as ICE core). ICE are one embodiment of a multivariate optical computing device, system, or component for performing analysis of a test sample. The test sample may represent any combination of liquids, gases, slurries, muds, polymers, multiphasic materials, hydrocarbon fluids, powders, and solids. The ICE cores may be utilized on testing samples in any number of phases, such as solids, liquids, gases, slurries, emulsions, powders, and multi-phase solutions.

The ICE cores may be utilized for detecting a number of properties in a test sample. The ICE cores may be utilized to assist in recreating the reservoir sample for performing characterization testing of the sample fluid in a laboratory environment. In another embodiment, a sample fluid may be generated by mixing fluids, gases, and solids to simulate any number of reservoir fluids. For example, a mixture may be created simulating a homogeneous fluid, single-phase fluid that may be present in a wellbore reservoir.

The ICE cores may also be utilized in any optical mode, such as absorbance, transmission, reflection, total internal reflection, fluorescence, Raman, Raleigh scattering, Brillion scattering, fiber optic, distributed fiber optic, and so forth. The ICE cores may have the same accuracy as laboratory quality optical spectrometers without using spectra, spectrometers, or conventional notch filters. The ICE cores may be utilized nondestructively, in situ, and in real-time. The ICE cores may be utilized in harsh environments, such as downhole conditions of a wellbore. The ICE cores may also be utilized in laboratories, sample equipment, containers, mobile equipment centers, impromptu workstations, or other locations or environments. In the illustrative embodiments, the ICE cores may be utilized in sample acquisition tools, transport vessels, and/or recombination vessels utilize in any number of "shakers" or agitators.

In one embodiment, the recombination process that controls the mixture and recombination of a sample fluid to an original state may be controlled in real-time. The original state of the fluid may be affected by any number of sample parameters, such as temperature, pressure, composition (e.g. gas blend, separator liquid, separator gas, solution gas etc.), mixture ratios (e.g. liquids, gases, sediments etc.), density, oil formation volume factor, viscosity, gas-oil ratio (GOR), gas fraction, interfacial tension, reservoir pressure, saturation pressure, and so forth.

The sample parameters are indicative of the parameters of the reservoir, pipe, or other sample location or environment when the sample is retrieved. The sample parameters may be taken at the time of sample, beforehand, or afterwards. The sample parameters may be determined utilizing any number of integrated sensors, logging tools, measurement devices, or so forth to duplicate the sample parameters when recombining the liquid sample to duplicate, approximate, or simulate the sample environment. For example, an ICE core integrated with, coupled to, or in communication with the recombination apparatus or system may measure the properties of the sample fluid in situ and in real-time to determine when a number of desired characteristics, thresholds, or parameters indicative of the original state are met.

In one embodiment, the optical signal taken by the ICE core may be communicated to a secondary device for determination of whether the composition and sample parameters are met. As a result, the secondary device may make the determinations and determine the composition of the sample fluid.

In another embodiment, an alert, message, or indication may be communicated from the optical sensor indicating that the sample parameters are met. The message may be sent directly or indirectly through a wireless connection (e.g. WiFi, Bluetooth, etc.), hardwired connection (e.g. Ethernet, LAN, serial connection, USB, etc.), or through one or more networks. The alert may be received by the agitator, a computing or communications device, or other system, device, or equipment.

As a result, the time and efforts required to meet the recombination parameters of the original state may be significantly reduced. For example, the status of the sample may be determined without utilizing external testing equipment. The results may then be more quickly available to make important decisions (e.g. determine whether continue drilling or developing a particular wellbore, adjust or modify exploration techniques and processes, and determine the status of a well).

In one embodiment, an optical sensor system may include an energy source, a detector, and at least one ICE core. The optical sensor may be coupled to a recombination, transfer, or fluid sample vessel. In one embodiment, the sensor may be integrated with the sample vessel or other internal component of the sample vessel, such that the sensor is in contact with the fluid during the recombination process. The contact may be constant or varying. For example, as the vessel is agitated by rocking, shaking, stirring or otherwise moving the sample fluid, the fluid may move from one end of the vessel to the other thereby interacting with the optical sensor. The sensor may take a reading and the optical signal may be converted into a property of interest, such as concentration. A second sensor may also be affixed to an opposite and/or internal component of the vessel to similarly monitor the composition of the sample. As a result, the recombination process may be stopped once both of the sensors detect an acceptable composition or state of the sample.

In another embodiment, the optical sensor may be integrated into a stirring arm, ball, mixing piston, or a freely moving component within the vessel. The sensor may be able to monitor all or portions of the sample as it moves through the vessel during the recombination process.

As previously noted, in situ and real-time monitoring of the recombination process may indicate when recombination is complete thereby eliminating unnecessary mixing as well as providing potentially valuable information about the compositional analysis, not only of the recombined fluid, but of the fluid(s) as it is mixing. This may eliminate the need for time-consuming analytical tests on a sub-sample from the vessel to determine the composition.

Figure 1:
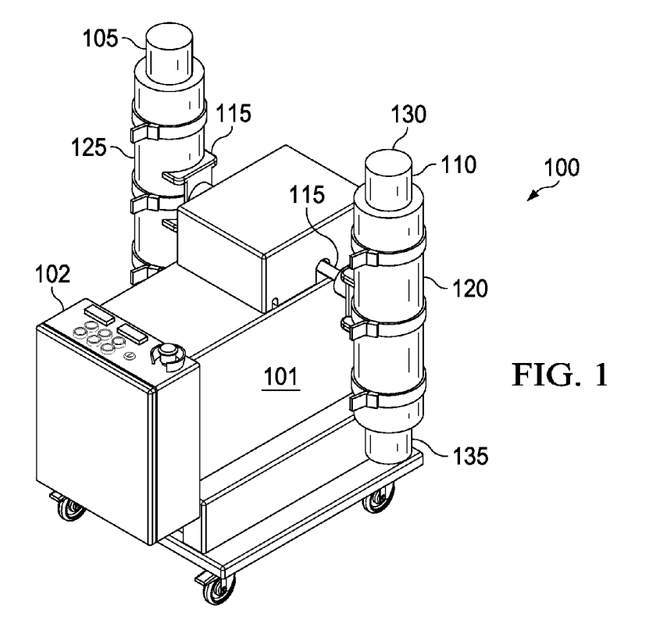
FIG. 1 is a schematic, perspective representation of a recombination agitator in accordance with an illustrative embodiment.

FIG. 1 is a pictorial representation of a recombination agitator 100 in accordance with an illustrative embodiment. Natural resource optimization may often begin with characterization of the reservoir fluid. Deficient sampling methods may lead to erroneous conclusions regarding the fluids and exploitation strategies that may be utilized to retrieve the fluids. In addition, if the sample fluid is not properly recombined, the associated testing may be inaccurate or altogether wrong. Bottomhole fluid samples may require accurate analysis in order to infer the appropriate information about the reservoir system.

In one embodiment, the recombination agitator 100 may be utilized to determine performance characteristics of the reservoir fluid or sample thereof. In some instances, it is impossible to measure the performance characteristics of the reservoir fluid downhole. Instead, a retrieve sample must be transported to a laboratory (e.g. facility, mobile, etc.) to re-create the sample parameters and then determine the performance characteristics of the reservoir fluid based on the sample. Performance characteristics may include any number of analytics, measurements, or determinations, such as density, formation volume factor, viscosity, interfacial tension, gas-oil ratio, compressibility, relative permeability relationships, and so forth utilized to determine an oil recovery strategy.

The recombination agitator 100 is utilized to re-create the phases and state of the reservoir fluid utilizing the sample in a laboratory setting. The phase or phases of the sample fluid may have transitioned during the transportation process (i.e. transportation of the fluid from downhole to a surface level laboratory setting). The recombination agitator 100 may be utilized to duplicate the sample parameters present in the reservoir including at least pressure, temperature, and GOR. The recombination agitator 100 may be configured to operate for a matter of seconds to a matter of days in order to reach the sample parameters and ensure that the sample fluid is satisfactorily recombined.

The recombination agitator 100 may also be utilized to create new fluids. For example, a mixture of liquids, gases, and/or solids may be combined and then agitated until it becomes a single-phase homogeneous fluid to perform any number of characterization tests or other experiments that may be applicable to reservoir or wellbore conditions.

In one embodiment, the recombination agitator 100 may include any number of integrated or externally attachable components, containers, interfaces, or so forth. In one embodiment, the recombination agitator 100 may be configured with a frame 101, controller 102, sample cylinders 105 and 110, rocker 115, heating mantles 120 and 125, and optical sensors 130 and 135.

The frame 101 may be configured to secure the different components of the recombination agitator 100. In one embodiment, the recombination agitator 100 may include any number of metal, plastic, or other components or framework for securing or enclosing the various mechanical, electrical, and structural components of the recombination agitator 100 during utilization. The frame 101 may also include wheels or attachment means for moving the recombination agitator 100 or securing it in place.

The controls 102 may include any number of components that are not specifically called out. For example the controls 102 may include any number of displays, adjustment levers or knobs, computing or communications interfaces (e.g. WiFi, Ethernet, software interface to a server or personal computer), power supplies, agitator motors (e.g. drive shafts, fuses, limiters, etc.), safety switches, fuses, pressure pumps, and so forth. Any number of electrical or physical connections may be made between the sample cylinders 105 and 110 and the controls 102 or other portions of the recombination agitator 100. For example, a high pressure pump (not shown) may pressurize the sample cylinders 105 and 110 to selected temperatures. In another embodiment, the sample cylinders 105 and 110 may include pressure regulation components for increasing or decreasing the pressure imposed upon the sample fluid. The controls 102 may include any number of analog or digital displays or read outs for receiving user input and providing information related to the performance of the controls 102, such as pressure, temperature, revolutions per minute, sheer forces, and so forth.

The sample cylinders 105 and 110 are sealed containers or vessels for storing, transporting, and/or agitating the sample fluid. The sample cylinders 105 and 110 may include any number of ports, valves, end caps, for introducing an optical sensor, pressurizing the sample cylinders, providing power to an internal stirring component (e.g. pistons, arms, etc.), operating heating components, injecting fluids or gases, and so forth. The sample cylinders 105 and 110 may include protrusions, an uneven surface, or other internal structures on the inside walls or edges of the sample cylinders 105 and 110 to disrupt the linear flow of the sample fluid and to enhance the mixing of the sample fluid within the sample cylinders 105 and 110. For example, additional fluids or gases may be introduced into the sample cylinders 105 and 110 utilizing needle valves or other valves to duplicate the sample parameters. The sizes and shapes of the sample cylinders 105 and 110 may vary based on the sample size and the requirements of the user.

The rocker 115 is configured to move or agitate the sample cylinders 105 and 110. In one embodiment, the rocker 115 may rock the sample cylinders 105 back and forth vertically, horizontally, or utilizing a number of different angles (static or dynamic). The rocker 115 may be configured as a dual action rocker because of its ability to agitate both of these sample cylinders 105 and 110 at the same time. The rocker 115 may also spin, roll, shake, vibrate, or otherwise agitate the sample cylinders 105 and 110 to recombine the respective samples. The recombination agitator 100 may utilize logic or an algorithm known to best mix the fluid samples by transitioning between distinct motions, such as spinning and shaking.

The heating mantles 120 and 125 are heating elements configured to heat the sample cylinders 105 and 110 to a desired temperature. In one embodiment, the heating mantles 120 and 125 may be wrapped around all or portions of the sample cylinders 105 and 110. In other embodiments, the heating mantles 120 and 125 may be configured to receive the sample cylinders 105 and 110 entirely. The heating mantles 120 and 125 may also be integrated with the sample cylinders 105 and 110 for producing the desired temperature within the sample cylinders 105 and 110. For example, the heating mantles may utilize resistive heating to uniformly heat the sample cylinders 105 and 110 to a temperature that is set and controlled by the controls 102. For example the heating mantles 120 and 125 may be configured to heat the sample cylinders 105 and 110 to 200° C. or more. The heating mantles 120 and 125 may be physical attached to the rocker 115 utilizing straps, connectors, ports, threads, buckles, inserts, or other mechanical fastening components.

In one embodiment, the optical sensors 130 and 135 are integrated in the end caps of the sample cylinders 105 and 110. However, the optical sensors 130 and 135 may be positioned anywhere within the sample cylinders 105 and 110. The optical sensors 130 and 135 may also be attached to the sample cylinders 105 and 110 or inserted into the sample cylinders 105 and 110. The optical sensors 130 and 135 may be configured to take measurements when fully immersed or contacting the sample fluids, at specific time or intervals, or based on other conditions or logic that are established. The optical sensors 130 and 135 may also be configured to send an alert or communications indicating the status of the sample fluids, including composition, density, optical measurements, GOR, and so forth. In one embodiment, the optical sensor 130 and 135 may constantly take measurements. In another embodiment, the optical sensors 130 and 135 may make periodic measurements of the sample fluids or may utilize logic or algorithms to increase or decrease the sample times.

The optical sensors 130 and 135 include ICE cores utilized to determine concentrations of fluid components. The ICE are specially designed filters that may separate an optical signal into an analyte signal that is proportional to the concentration of the analyte being examined. The combination of the optical sensors 130 and 135 with the sample cylinders 105 and 110 may allow the recombination agitator 100, or interconnected or communicating system, device, or user to know that the mixing is sufficient or complete. The mixing time required in the laboratory may be reduced significantly to only the mixing time that is necessary to achieve the desired recombination. In addition, in-situ real-time compositional analysis performed by the optical sensors 130 and 135 may alleviate the need for post-experiment analytical analysis on a sub-sample of the sample fluid to determine composition or compliance with the sample parameters.

In one embodiment, the optical sensors 130 and 135 may be integrated with the sample cylinders 105 and 110. As a result, modifications may not be required to the recombination agitator 100. Instead, the sample cylinders 105 and 110 may be specially configured to provide status information of the sample fluids based on ongoing measurements of the ICE cores of the sample cylinders 105 and 110. In addition, the sample cylinders 105 and 110 may be shaped and configured to be received by any number of standard recombination or restoration apparatuses. Many companies or users may also build or assemble their own recombination agitators to fit their respective needs and requirements.

In another embodiment, the optical sensors 130 and 135 may be configured as an add-on part for the sample cylinders 105 and 110. For example, the optical sensors 130 and 135 may represent end caps, of the sample cylinders 105 and 110 that may replace the default end caps that come with the sample cylinders 105 and 110 as produced. The optical sensors 130 and 135 may also be integrated within valve inserts, side walls, window attachments, or other components of the optical sensors 130 and 135. In one embodiment, the optical sensors 130 and 135 may include a wireless transceiver to communicate their respective measurements to one or more computing or communications devices.

In other embodiments, the optical sensors 130 and 135 may be integrated within a viewing window of the sample cylinders 105 and 110. The optical sensors 130 and 135 may also be integrated within a piston, cylinder, or ball integrated with or free-floating within the sample cylinders 105 and 110. In one embodiment, the optical sensors 130 and 135 may include a wired connection or antenna that extends from the sample cylinders 105 and 110. The wired connection or antenna may be utilized to communicate the optical measurements taken by the optical sensors 130 and 135.

Figure 2:
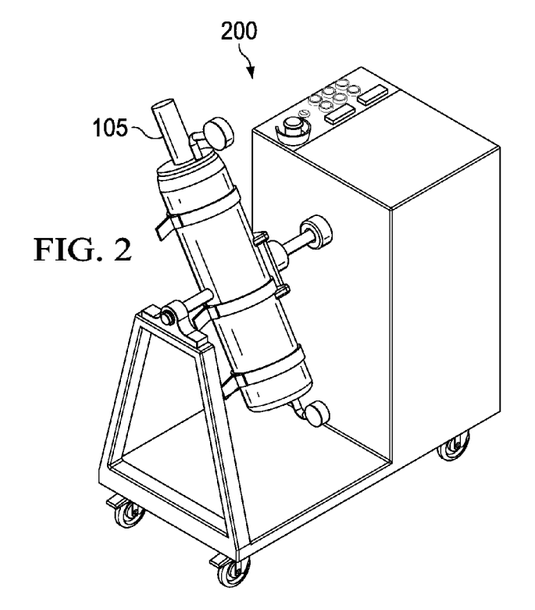
FIG. 2 is a schematic, perspective of another recombination agitator in accordance with an illustrative embodiment.

FIG. 2 is a pictorial representation of another recombination agitator 200 in accordance with an illustrative embodiment. The recombination agitator 200 may include the components of the recombination agitator 100 of FIG. 1. However, the recombination agitator 200 may be configured to agitate a single sample cylinder 105, instead of multiple sample cylinders. The recombination agitator 200 may shake, rock, spin, vibrate, or otherwise agitate the sample cylinder 105.

Figure 3:
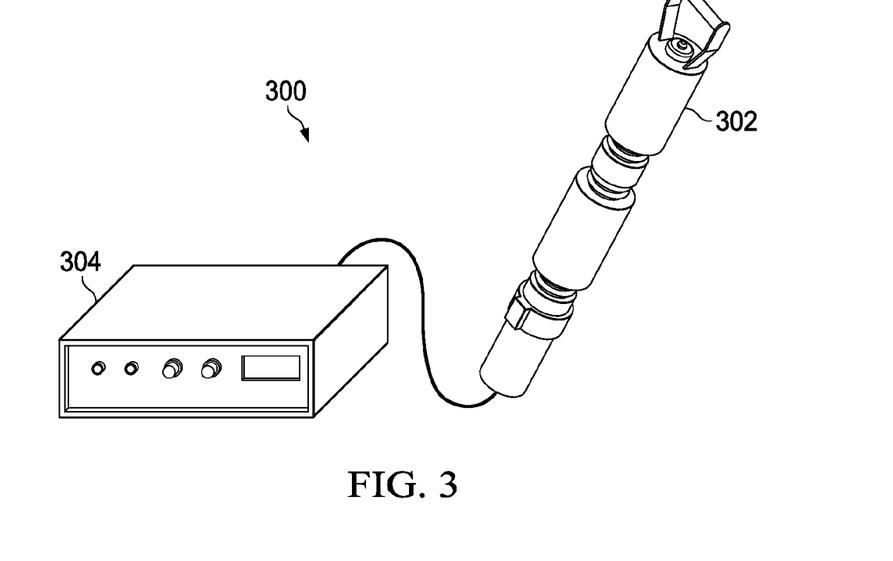
FIG. 3 is a schematic, perspective of another recombination agitator in accordance with an illustrative embodiment.

FIG. 3 is a pictorial representation of another recombination agitator 300 in accordance with an illustrative embodiment. The recombination agitator 300 may be configured to perform all of the functions of the recombination agitators 100 or 200 of FIGS. 1 and 2, respectively. In one embodiment, the recombination agitator 300 may include a sample cylinder 302. The sample cylinder 302 may be configured to perform agitation of the sample fluid, heat or cool the sample fluid, increase or decrease the sample fluid, and perform the optical measurements. The recombination agitator 300 may also include a controller 304 that provides power to agitating components, such as mixers, pistons, vibrators, or other components within the sample cylinder 302. An optical sensor may be integrated within end caps or separators of the sample cylinder 302 or within the sample cylinder 302 as previously described. The sample cylinder 302 may also be configured to regulate pressure and temperature of the sample fluid.

Figure 4:
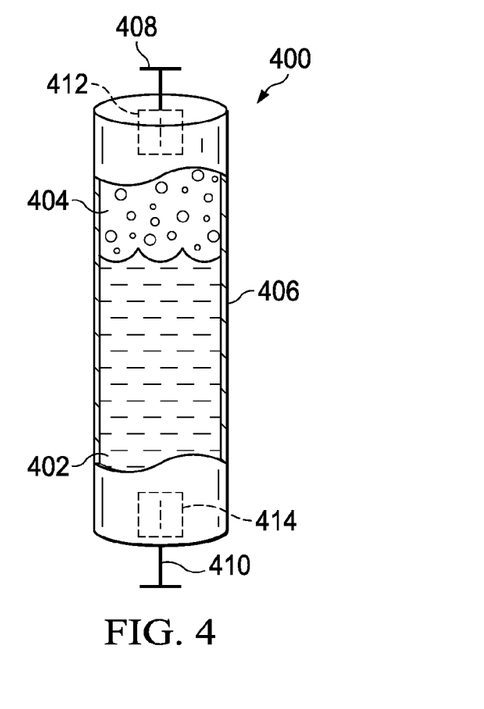
FIG. 4 is a schematic, side view of a recombination vessel utilizing an optical sensor in accordance with an illustrative embodiment.

FIG. 4 is a pictorial representation of a recombination vessel 400 utilizing an optical sensor in accordance with an illustrative embodiment. In one embodiment, the recombination vessel 400 may be utilized to recombine a sample fluid 402. The recombination vessel 400 may also include any number of gases 404. The recombination vessel 400 may include any number of components including sidewalls 406, end caps 408 and 410, and optical sensors 412 and 414.

As previously described, the optical sensors 412 and 414 may be integrated with the end caps 408 and 410 of the recombination vessel 400. The recombination vessel 400 may be moved, rotated, spun, and vibrated such that the position of the liquid 402 and the gas 404 may vary in time. As a result, the optical sensors 412 and 414 are positioned to take measurements of the liquid 402 (and the gas 404 if needs be) at different positions of the recombination vessel 400.

Although not explicitly shown, the optical sensors 412 and 414 may include a power source (e.g. battery, power connection, etc.), ICE core, and transceiver for communicating the optical measurements taken by each of the optical sensors 412 and 414. The optical sensors 412 and 414 may also communicate with one another to determine whether preset sample parameters corresponding to a reservoir condition and environment are met.

The recombination vessel 400 may be configured to adjust the pressure and temperature of the sample fluid 402 and the gases 404 within the recombination vessel 400 based on integrated controls of the recombination vessel 400 or based on external stimuli or components. The recombination vessel 400 may include ports or valves for being pressurized by a pump, retrieving fluid samples, and/or injecting additional fluids or gases. As previously noted, the end caps 408 and 410 including the optical sensors 412 and 414 may be the default end caps or may be purchased separately.

Figure 5:
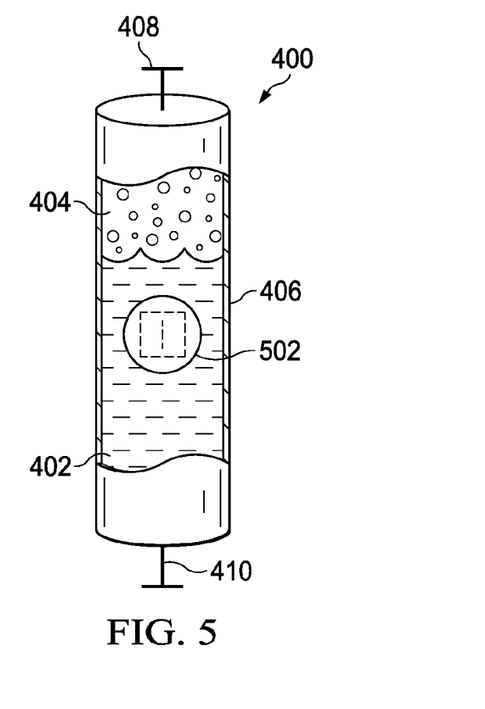
FIG. 5 is a schematic, side view of another recombination vessel utilizing an optical sensor in accordance with an illustrative embodiment.

FIG. 5 is a pictorial representation of another recombination vessel 500 utilizing an optical sensor in accordance with an illustrative embodiment. The recombination vessel 500 may include many of the components of the recombination vessel 400 of FIG. 4. The recombination vessel 500 may include an optical sensor 502. The optical sensor 502 may be configured to move freely within the recombination vessel 502 help mix the sample fluid 402 and the gases 404 and to take optical measurements at the same time.

In one embodiment, the optical sensor 502 may be partially encased in a case or cover that protects various components of the optical sensor 502. For example, only a portion of the ICE core may be exposed to the sample fluid 402 and gases 404 to take optical measurements.

In another embodiment, the optical sensor 502 may be attached to a fiber optic cable fed into the recombination vessel 500. The fiber optic cable may be sealed off to prevent unwanted leakage or contamination. The optical sensor 502 may also be integrated with a side wall, high pressure window, or other component of the recombination vessel 500.

In one embodiment, the optical sensor 502 may indicate when the sample fluid is within a threshold associated with the sample parameters. For example, the sample parameters may indicate that the sample fluid is at a desired temperature, pressure, and GOR associated with composition. The threshold may include a minimum and maximum for all or a portion of the sample parameters.

Figure 6:
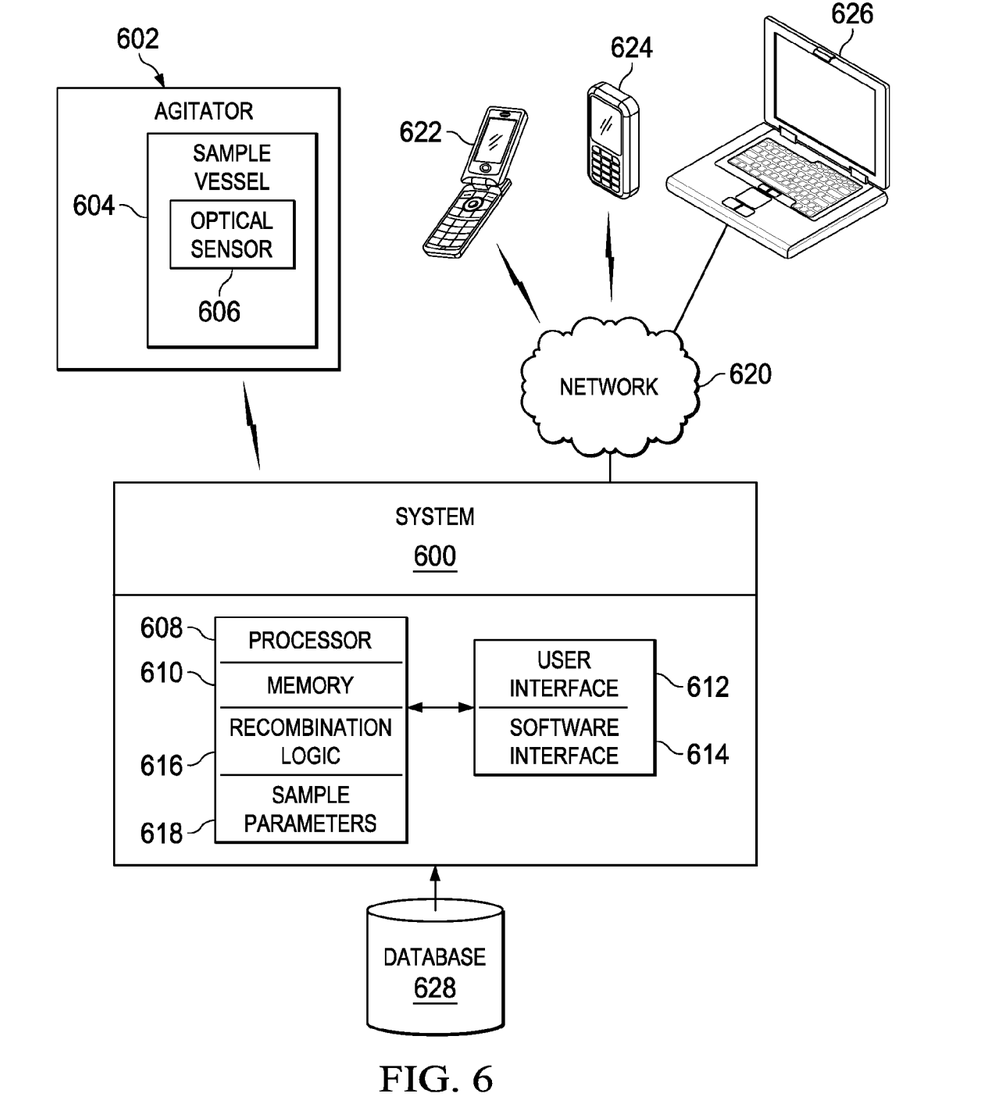
FIG. 6 is a block diagram of a system for performing recombination of a sample in accordance with an illustrative embodiment.

FIG. 6 is a block diagram of a system for performing recombination of a sample in accordance with an illustrative embodiment. FIG. 1 is a schematic diagram of a system 600 or apparatus for monitoring test samples from a natural resource environment by employing in situ optical analysis device. The in situ optical analysis may be performed utilizing an agitator 602 including a sample vessel 604 and an optical sensor 606.

In one embodiment, the system 600 may be utilized to determine a number of parameters or properties of test samples (e.g. crude petroleum, water, mixtures, liquids, etc.) either downhole in a drilling well, laboratory, pipeline, or other environment. The term "downhole" means located in a well or a stream connected to a well or connected to any of one or more reservoirs whose fluids are subject to being pumped to the surface at a well. In practice, numerous reservoirs may be interconnected by a web of streams all feeding a common well head. The term pipeline means a pipe employed to convey petroleum from a field well head to a remote location. Pipes are employed downhole and in pipelines. The term "pipe" includes downhole pipes or pipeline pipes. Downhole pipes may be vertical, horizontal, or have other spatial relationships.

The determined parameters may be utilized for analysis, to determine petroleum flow, or analysis of applicable mixtures and materials, and other relevant determinations. The term "parameters" means chemical or physical characteristics, composition, properties, or elements contained in the test sample (i.e. petroleum or which forms the petroleum composition) and which includes, but is not limited to SARA (saturates, asphaltenes, resins, aromatics), solid particulate content such as dirt, mud, scale and similar contaminants, porosity, pH, total dissolved solids, ionic content (i.e., $H_2O$ ion-composition and content), hydrocarbon composition and content, gas composition C1-C6+ and content, $CO_2$, $H_2S$ and correlated pressure volume temperature (PVT) properties including GOR, bubble point, density, particle shape, particle distribution, and viscosity among other properties. For example, crude petroleum may include aromatics, resins, asphaltenes, and saturates.

System 600 may include apparatuses located at and in contact with flowing crude petroleum and which components are located downhole or on a pipeline to determine in real time the sample parameters, such as temperature, pressure, GOR, density, composition, as well as the other properties of the petroleum which is flowing in pipes underground or in the pipeline. For example, the optical sensor 606 may be integrated in a capture device or tool that captures the sample fluid from a reservoir. As a result, the apparatuses of the system 600 may be subject to the extreme temperatures and pressures of the underground streams, but yet does not employ costly spectroscopic instruments as used in the prior art system, but rather rugged reliable optical analysis devices, such as ICE cores.

In one embodiment, the system 600 may be utilized for real-time analysis of test samples during recombination in a mobile or home facility, sample container, or other location or container after retrieval of the test sample. For example, an agitator 602 may be configured to recombine a liquid sample within the sample vessel 604 based on optical measurements taken by the optical sensor 606 The optical sensor 606 includes the ICE core.

In one embodiment, the system 600 may be integrated with the agitator 602. In another embodiment, the agitator 602 or optical sensor 606 may be controlled by or communicate with the system 600. The system 600 or agitator 602 including the optical sensor 606 may also be managed by or communicate with the electronic devices 622, 624, and 626. The communications may occur directly through a wired or wireless connection or through one or more networks. The sample vessel 604 or agitator 602 may alternatively include any or all of the components of the system 600. For example, the optical sensor 606 may include an application-specific integrated circuits (ASIC), field-programmable gate array (FPGA), processor and memory, or other logical components for performing all of the functions and processes of the system 600.

In one embodiment, system 600 may be a computing device including a microprocessor 608, memory 610 which may include one or more static or dynamic memories or caches (e.g. hardrive, read-only memory (ROM), random-access memory (RAM), etc.) for storing the analysis program and operating system program and determined data among other information as known in the art of spectral analysis as understood by one of ordinary skill. The system may include a user interface 612 for receiving user input, selections, and feedback. For example, the user interface may include a display, a keyboard, a mouse, and/or other peripheral components.

The system 600 may also be configured to communicate with any number of other devices or software applications through the software interface 614. For example, the software interface 614 may be configured to receive information, such as sample parameters from users, devices, components, or systems in the field or in different locations. The software interface 614 may interact with any number of engineering programs, mobile applications, web browsers, or so forth to allow access and management of the system 600 or the data and information stored therein. For example, the software interface 614 may communicate with programs, such as Engineers Desktop, Engineers Data Model (EDM) Open Wells, OpenWorks® from Landmark Graphics Corporation, Data Analyzer, Engineers Data Model, MatLab, LabWorks, and other similar platforms.

The microprocessor 608 is circuitry or logic enabled to control execution of a set of instructions. The processor 608 may be one or more microprocessors, digital signal processors, ASIC, central processing units, or other devices suitable for controlling an electronic device including one or more hardware and software elements, executing software, instructions, programs, and applications, converting and processing signals and information, and performing other related tasks. The processor 608 may be a single chip or integrated with other computing, communications, exploration devices, downhole tools.

The memory 610 is a hardware element, device, or recording media configured to store data for subsequent retrieval or access at a later time. The memory 610 may be static or dynamic memory. The memory 610 may include a hard disk, random access memory, cache, removable media drive, mass storage, or configuration suitable as storage for data, instructions, and information. In one embodiment, the memory 610 and processor 608 may be integrated. The memory may use any type of volatile or non-volatile storage techniques and mediums.

The system 600 may also include recombination logic 616 and sample parameters 618. The recombination logic 616 may represent digital logic, software, firmware, or a combination thereof utilized to determine whether the liquid sample within the sample vessel 604 has met the sample parameters 618. The sample parameters 618 are the data, information, properties, and characteristics associated with the reservoir or environment in which the liquid sample was retrieved. The sample parameters 618 may be retrieved utilizing any number of measurement tools, ICE cores, transfer vessels, sensors, or so forth.

In one embodiment, the sample parameters 618 may be automatically uploaded to the system 600 through a network 620. For example, the sample parameters 618 may be uploaded utilizing an identifier associated with the wellbore and other relevant information, such as location, depth, date, how retrieved, sampling party, sampling equipment, and so forth.

In another embodiment, the sample parameters 618 may be uploaded by one or more users utilizing an electronic device such as electronic devices 622, 624, and 626. The electronic devices 622, 624, and 626 may represent any number of computing or communications devices including cell phones, PDAs, smartphones, laptops, tablets, e-readers, players, and other forms of personal, business, industrial, or consumer electronic devices. In one embodiment, the system 600 is located at central location remote from the agitator 602. However, the communications of the different devices and components of FIG. 6 may be connected and configured to be performed directly or indirectly.

In another embodiment, the recombination logic 616 and the sample parameters 618 may be included within the optical sensor 606 allowing for autonomous operation of the agitator 602. As a result, the liquid sample may be agitated and the sample parameters 618 duplicated until the liquid sample reaches the desired state in order to perform any number of characterization and sample tests. An alert or other message may be sent by the optical sensor 606 to any of the sample vessel 604, agitator 602, system 600, and/or electronic devices 622, 624, and 626.

The sample vessel 604 may include any number of optical sensors 606. While one device is shown, the number of optical sensor is shown by way of illustration and more optical sensor may be used in practice. For example, optical sensor 606 may be positioned in the ends or middle of the sample vessel 604 and may be utilized for detecting and analyzing light interacted with the associated sample fluid. The optical sensor 606 may measure multiple properties or a single property of the sample fluid as needed. For example, the optical sensor 606 may include a number of ICE cores each configured to sense a distinct property. As a result, the optical sensor 606 may be utilized in combination to provide an overall picture of the recombination of the sample fluid within the sample vessel 604.

The optical sensor 606 is rugged and may be configured to withstand the temperatures and pressures in situ within the sample vessel 604 of the agitator 602 and may be placed for long term or permanent use. The optical sensor 606 may be a marked improvement over present analyzing systems which may be bulky, slow, and/or require extracting fluid from within the sample vessel 604 to determine the recombination status of the sample fluid. In addition, the optical sensor 606 is rugged and may be configured to automatically determine whether the sample fluid has met various sample parameters (i.e. is indicative of the reservoir fluid where sampled). The optical sensor 606 may be manufactured for longer term, shorter term, one time, or disposable use.

The number of optical sensors 606 in the system 600 depends on the requirements or preferences of one or more users, required analysis, size, shape, capabilities of the sample vessel, and the number of properties being monitored. Communications within the system 600 may occur in real-time or via any number of subsequent communications, data transfers, or synchronization processes. A user may also initiate a communication, test, analysis, or other process in response to a user selection or input to the system 600.

It is contemplated that the number of optical sensors 606 in communication with the system 600 is not limited to measuring the properties of a test sample at a single location. The system 600 may be programmed to communicate with or monitor a large number of optical sensors 606 associated with and located in respect of a number of different locations. Thus, the properties of a test sample may be monitored simultaneously by the system 600 which may also be programmed to correlate a number of different properties as being related to a flow assurance problem in one reservoir system. The system 600 may represent one or more computing or communications devices, systems, equipment, or components.

The communications within the system 600 may occur directly or through one or more networks including, a publicly switched telephone network, cell or wireless networks (e.g. 3G, 4G, LTE, PCS, GMSR, etc.), Ethernet networks, or so forth.

In one embodiment, the optical sensors 606 may also monitor fluid samples within pipes, streams, reservoirs, and wellbores to give a picture of the petroleum and other test samples flowing, stored, or being retrieved. As a result, the optical sensor 606 may monitor a number of properties instantaneously or at the convenience of one or more users. As a result, problems or issues may also be efficiently monitored, detected, and logged to take any number of corrective actions for a reservoir, stream, pipeline, or so forth. One or more thresholds may be utilized for distinct properties to perform more thorough analysis or perform different tests.

The optical sensor 606 may be relatively low cost and rugged and may be implemented in many more locations and streams than otherwise possible with other systems. In one embodiment, the optical sensor 606 (described as a representative device may include a battery, a light source, a test sample being monitored, an ICE core operating an optical regression calculation device), a detector for detecting light reflected from the ICE core and a detector for detecting the light transmitted by ICE core. The ICE core is a unique optical calculation device that comprises multiple layers specially sized, shaped, and configured to determine properties of the test sample.

In one embodiment, the characterization testing performed on the liquid sample within the sample vessel 604 may be stored in a database 628. The database may communicate with the system 600 and may include information related to users, companies, exploration, wellbores, sample parameters, agitator configuration, and so forth. The database 628 may also back up the information stored within and flowing through the system 600 for subsequent retrieval or access.

Figure 7:
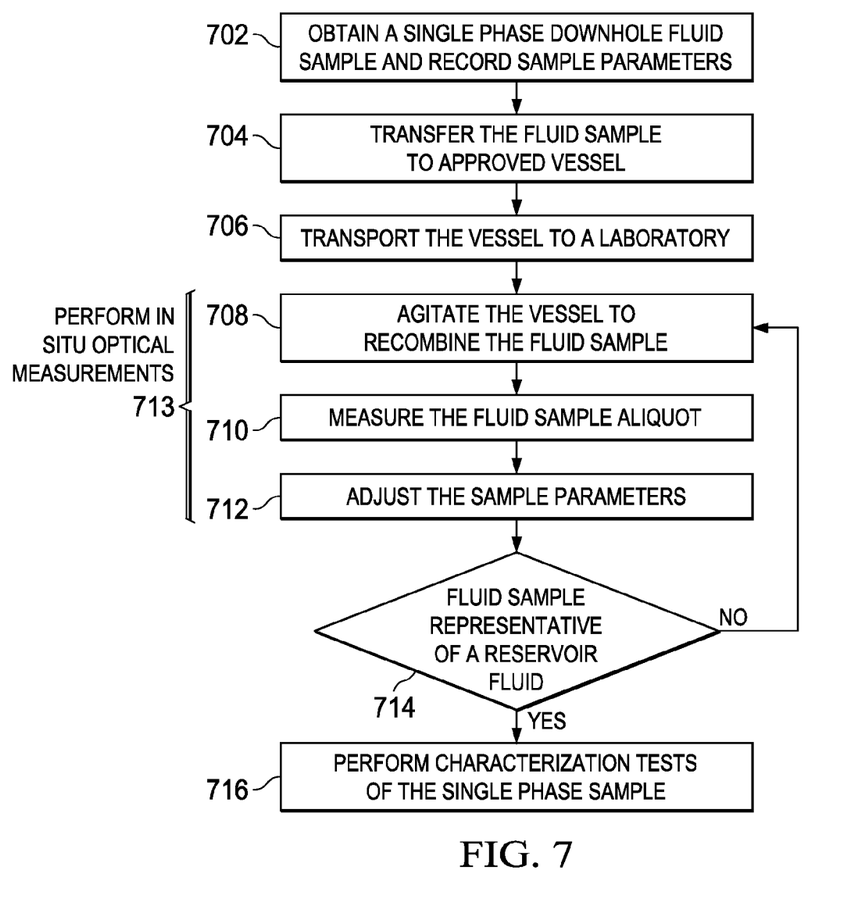
FIG. 7 is a flowchart of a process for performing recombination of a sample utilizing an optical sensor in accordance with an illustrative embodiment.

FIG. 7 is a flowchart of a process for performing recombination of a sample utilizing an ICE core in accordance with an illustrative embodiment. In one embodiment, the process of FIG. 7 may be implemented by a system including an ICE core configured for optical analysis of a sample. The process may begin with the system obtaining a single phase downhole fluid sample and recording sample parameters (step 702). Although described as a downhole fluid sample, the sample may be obtained in any environment or conditions (e.g. downhole, above ground, external pools, etc.). The sample may similarly include any number of fluids, gases, solids, slurries, gels, mixtures, or combinations thereof whether in a single phase or multi-phase.

In one embodiment, the sample parameters are the conditions, factors, or parameters that describe or are indicative of the sample environment (where the samples are taken), including, but not limited to, pressure, temperature, gases, boundary composition, and so forth. The sample may be obtained utilizing any number of mechanical, electromechanical, remote, and/or robotic devices, components, or systems. In one embodiment, an ICE core may be integrated with the sample device to determine the original composition, mixture, or state of the single phase sample.

Next, the system transfers the sample to an approved vessel (step 704). The sample may be acquired as part of a drill string, extraction device, logging while drilling (LWD) tool, measurement while drilling (MWD) tool, or other sample or analysis tool. In one embodiment, the sample may be acquired within the vessel utilized as a transport container. In another embodiment, the sample may be transferred from a first vessel to a second vessel utilized for transport. The vessel(s) utilized in the process of FIG. 7 are configured to prevent unwanted contamination to the sample during the extraction and transfer process. During steps 702 and 704 the sample fluid may undergo phase separation. For example, the original fluid sample may separate into distinct components based on changes in the environment and other conditions within the sample vessel. The term sample vessel as herein described may represent the transport vessel, the sample vessel utilized for recombination, and/or other vessels utilized to retrieve, transport, recombine, and analyze the sample fluid.

Next, the system transports the vessel to a laboratory (step 706). The laboratory may be a standard facility, mobile laboratory located proximate the wellbore, or any number of other locations or facilities where samples are analyzed. In one embodiment, the vessel may be maintained at or as close as possible to the sample parameters (e.g. pressure or temperature) to duplicate or mimic the downhole conditions where the sample was obtained. For example, the vessel may include a heater or temperature element and pressure (e.g. pressure sensors, pump, etc.) controls for maintaining a desired temperature and pressure.

Next, the system agitates the vessel to recombine the fluid sample (step 708). In one embodiment, the vessel utilized for transport may be configured to be integrated with or attached to the recombination device or system. The sample vessel may be agitated through movement, rolling, spinning, vibration, shaking, mixing or other agitation processes. During steps 708-710, the system performs in situ optical measurements (step 713). The measurements may be performed utilizing the ICE core as previously described.

Next, the system measures the fluid sample aliquot (step 710). The fluid sample aliquot is measured utilizing an optical sensor including an ICE core. The fluid sample aliquot may represent a portion of the fluid sample that immerses, contacts, or is measured by the ICE core.

Next, the system adjusts the sample parameters (step 712). During step 712, the sample parameters are duplicated in the sample vessel to facilitate the desired recombination. In one embodiment, the sample parameters may be manually or automatically entered into the system and associated with the fluid sample. The sample parameters may be adjusted in real time to ensure that the fluid sample simulates or duplicates, as exactly as possible, the conditions in which the fluid was sampled from the reservoir. As previously disclosed, the sample parameters may include pressure, temperature, GOR, gas and liquid per sample unit (e.g. separator gas, calculated gas, solution gas, etc.), composition, bubble point pressure, and so forth.

Next, the system determines whether the fluid sample is representative of a reservoir fluid (step 714). For example, the system may determine that the fluid sample has reached a single phase consistent with the phase and state of the reservoir fluid when the fluid sample was originally obtained from the reservoir. In one embodiment, the fluid sample may be analyzed and measured to determine whether it is sufficiently similar to the reservoir fluid when originally sampled. In another embodiment the sample parameters may be duplicated or approximated as closely as possible to determine that the fluid sample is representative of the reservoir fluid.

If the system determines the fluid sample is representative of the reservoir fluid in step 714, the system performs characterization tests on the single phase sample (step 716). Characterization tests may include determining information, such as a relative mobility and permeability ratio between one or more gases and oil, viscosity, formation volume factor, viscosity, interfacial tension, GOR, composition of any number of liquids, gases (e.g. ethane, methane, nitrogen, butane, pentane, carbon dioxide, hydrogen sulfide, etc.), and solids within the sample fluid, molecular weight, and so forth. The characterization test may be utilized to assess and implement enhanced oil recovery strategies that are appropriate for the reservoir based on the characterization tests.

The characterization tests may include any number of analytical tests, including, but not limited to gas chromatography, mass spectrometry, PVT experiments, and so forth. The characterization tests may be performed by the optical sensor(s) or any number of external devices, systems, tools, or equipment.

If the system determines the fluid sample is not representative of the reservoir fluid in step 714, the system returns to perform steps 708-713.

The illustrative embodiments provide a system, method, and devices for determining when a sample fluid has been completely recombined, evaluating progress of the recombination process, and simultaneously determining the composition of the sample fluid. As a result, recombination time, efforts, and expenses are significantly reduced.

One embodiment provides a system, method, and sample vessel for recombining a sample fluid. The sample fluid is received in a sample vessel. Sample parameters are recreated in the sample vessel. The sample fluid is agitated within the sample vessel. Optical measurements of the sample fluid are performed within the sample vessel utilizing one or more optical sensors. A determination is made whether recombination is complete in response to the optical measurements of the sample fluid performed by the one or more optical sensors.

Another embodiment provides a system for performing recombination of a sample fluid. The system includes an agitator for agitating the sample fluid utilizing sample parameters. The system also includes one or more sample vessels attached to the agitator and securing the sample fluid during agitation. The one or more sample vessels include one or more optical sensors that determine a composition of the sample fluid and when the sample fluid meets the sample parameters.

Yet another embodiment provides a sample vessel. The sample vessel includes one or more removable end caps for receiving the sample fluid. The sample vessel further includes one or more optical sensors configured to indicate when recombination of the sample fluid is complete. The sample vessel is attachable to an agitator for agitating the sample fluid to facilitate recombination.

The previous detailed description is of a small number of embodiments for implementing the invention and is not intended to be limiting in scope. The following claims set forth a number of the embodiments of the invention disclosed with greater particularity.

What is claimed:

1. A method of determining whether recombination of constituents in a sample fluid is complete, comprising:
   receiving the sample fluid in a sample vessel;
   recreating original sample parameters in the sample vessel;
   agitating the sample fluid within the sample vessel;
   performing optical measurements of the sample fluid within the sample vessel utilizing one or more optical sensors; and
   determining whether recombination of constituents in the sample fluid is complete in response to the optical measurements of the sample fluid performed by the one or more optical sensors.

2. The method according to claim 1, wherein the one or more optical sensors include at least an integrated computation element for optically measuring the sample fluid.

3. The method according to claim 1, wherein the original sample parameters comprise at least one of pressure, temperature, or gas-oil ratio.

4. The method according to claim 1, wherein the performing optical measurements further comprises determining a composition of the sample fluid.

5. The method according to claim 1, further comprising communicating the optical measurements to one or more devices for display to a user.

6. The method according to claim 1, further comprising:
   retrieving the sample fluid from a reservoir; and
   recording the original sample parameters of the reservoir where the sample fluid is captured.

7. The method according to claim 6, wherein the recombination is complete when the sample fluid approximates a reservoir fluid of the reservoir.

8. The method according to claim 1, further comprising performing characterization tests of the sample fluid in response to determining whether the recombination of the sample fluid is complete.

9. The method according to claim 1, wherein the recombination of constituents in the sample fluid is determined to be complete in response to the sample fluid reaching a single phase associated with the original sample parameters.

10. The method according to claim 1, wherein the one or more optical sensors indicates when the sample fluid meets a threshold associated with a reservoir fluid.

\* \* \* \* \*